(12) United States Patent
Brambila

(10) Patent No.: US 11,246,894 B2
(45) Date of Patent: Feb. 15, 2022

(54) SUPERFOOD SUPPLEMENT FOR DOGS AND ITS MANUFACTURING PROCESS

(71) Applicant: Aldo Gonzalez Rubio Brambila, Mexico City (MX)

(72) Inventor: Aldo Gonzalez Rubio Brambila, Mexico City (MX)

( * ) Notice: Subject to any disclaimer, the term of this patent is extended or adjusted under 35 U.S.C. 154(b) by 22 days.

(21) Appl. No.: 16/709,293

(22) Filed: Dec. 10, 2019

(65) Prior Publication Data

US 2020/0268814 A1    Aug. 27, 2020

(30) Foreign Application Priority Data

Feb. 22, 2019  (MX) .................. MX/A/2019/002142

(51) Int. Cl.
| | | |
|---|---|---|
| *A61K 35/747* | (2015.01) | |
| *A61K 35/744* | (2015.01) | |
| *A61K 9/00* | (2006.01) | |
| *A61K 35/00* | (2006.01) | |

(52) U.S. Cl.
CPC .......... *A61K 35/747* (2013.01); *A61K 9/0056* (2013.01); *A61K 35/744* (2013.01); *A61K 2035/115* (2013.01)

(58) Field of Classification Search
None
See application file for complete search history.

(56) References Cited

U.S. PATENT DOCUMENTS 5,968,569 A     10/1999  Cavadini et al.
2018/0343812 A1*  12/2018  Leo .................. A01G 22/00

OTHER PUBLICATIONS

Schmitz et al. Vet. Med. Sci. 2: 71-94, 2016.*

* cited by examiner

*Primary Examiner* — Sarvamangala Devi
(74) *Attorney, Agent, or Firm* — Thomas | Horstemeyer, LLP

(57) ABSTRACT

The present invention is an improved superfood supplement for dogs.

2 Claims, No Drawings

SUPERFOOD SUPPLEMENT FOR DOGS AND ITS MANUFACTURING PROCESS

FIELD OF THE INVENTION

The present invention is an improved superfood supplement for dogs.

BACKGROUND OF THE INVENTION

US Patent Document US 2009/0214499 A1 describes a probiotic nutritional supplement which has the specific purpose of treating diarrhea in felines and is composed of bacteria of the genus *Bifidobacterium*.

The fundamental difference of this patent with which we are proposing is that it is focused on felines, and ours focused on canines.

Also, the bacteria it uses belong to the genus *Bifidobacterium*, the dog food we propose will not have any bacteria belonging to that genus, ours are mostly from *Lactobacillus* and one from *Enterococcus*; These are very different microorganisms.

The disadvantage that it with the compared document is that, it does not specify if the supplement will be presented in dry or wet form, but by the description of the product it can be inferred that it is in dry form; although they imply that they are live bacteria, they are probably lyophilized; The bacteria that our dog food will have will not be lyophilized, it will only be refrigerated and in the presence of a natural conservative to reduce their metabolic activity.

Another important difference is that it is specifically designed to treat diarrhea, however, the dog food will have several much more important functions.

Probably, if the dog presents a current episode of diarrhea it will be reduced, but it will be more of a side effect of consuming the food. It is also inferred that the product is only a nutritional supplement, rather than what we are proposing, which is a complete food that provides a complete diet for an adult dog of 15 kg and it also includes stabilizing probiotics of the canine intestinal flora.

As for the similarities, it is a dietary supplement that seeks to improve the intestinal health of pets from the use of orally administered probiotics.

U.S. Pat. No. 5,968,569 A describes a "treat" for dogs consisting of dry food that has inside a semi-solid gel matrix in which probiotics are suspended.

The most important differences are the presentation of the food, the presentation of the prebiotic, the nutritional content of the treat and the bacterial species employed.

This is a dry product that has the function of being some kind of reward, it is not a food per se, so its nutritional content is lower than that of our product.

Also, since it is a dry food, the way to present probiotics is in a semi-solid gel matrix, on the other hand, since our product is a wet food, bacteria are suspended throughout the product.

Another difference is that they use *Lactobacillus subtillis*, however, other bacterial species are used in the present invention, which, although they are part of the genus *Lactobacillus*, are different strains and their role in the canine intestine is distinct, so the expected effect in the health and balance in the gastrointestinal tract of the animal will be of another nature.

BRIEF DESCRIPTION OF THE INVENTION

The product consists of an improved superfood supplement for dogs which will provide the complete nutrition that an adult dog of 15 kilos needs to maintain an integral well-being (vitamins, minerals, proteins, essential fats, calories and fiber), the product comprises the four Probiotics mentioned below:

*Lactobacillus salivarius*
*Lactobacillus fermentum*
*Lactobacillus rhamnosus*
*Enterococcus faecium*

These microorganisms are not presented in lyophilized form to ensure greater efficacy in the gastrointestinal tract and will be present in an abundance of $1 \times 10^8$ CFU/g.

DETAILED DESCRIPTION OF THE INVENTION

The concerned issue is that dogs are not obtaining complete nutrition from adequate sources, therefore an imbalance in the microbiota of their GIT is provoked, this results in multiple health issues of different natures, such as dermal, inflammatory, parasitic and others related to the immune system and pyrogenic agents. The solution to this problem is the creation of an improved superfood supplement for dogs added with probiotics.

The present superfood is composed of ingredients of natural origin and four bacteriological strains, which are presented below:

The ingredients are:
Carrots: 30 g
House cricket (*Gryllodes sigillatus*) 36 g
Beef, 20% fat 20 g
Cow liver 70 g
Brown rice 30 g
Peas 28 g
Oatmeal 28 g
Potato 50 g
Spinach 28 g
Pumpkin 30 g The nutritional content of these ingredients is complemented with supplements of vitamin A, vitamin C, vitamin D, vitamin E, vitamin K, thiamine, riboflavin, niacin, vitamin B6, B5, B12, folic acid, calcium, iron, phosphorus, iodine, magnesium, zinc, copper, manganese and selenium.

The total nutritional content of a serving (350 g) of the superfood contains:
50.2 grams of protein
15 grams of fat
10.5 grams of fiber
7 mg of Vitamin B1
9.7 mg of Vitamin B2
5 mg of Vitamin B6
266 micrograms of Vitamin B9
24 mg of Vitamin B3
89 micrograms of Vitamin B12
9 mg of Vitamin B5
8 mg of Vitamin K
40 mg of Vitamin C
12 mg of Vitamin A
9 mg of Vitamin E
16 mg of Zinc
11 mg of Iron
800 mg of Phosphorus
250 mg of Sodium
350 mg of Choline
7 micrograms of Fluor
590 mg of Omega 3
2500 mg of Omega 6
1500 mg of Potassium 13 mg of Copper
2 mg of Manganese
160 mg of Magnesium
900 mg of Calcium
100 micrograms of Iodine
50 mg of Selenium This results in the complete nutritional content that a 15 kg adult dog of a medium breed needs, the portions are scalable for larger or smaller canines.

The product contributes a total of 500 Kcal and has an approximate water content of 70% (±5%)

To create the final product, all the elements are combined and ground to create a paste of pureed consistency, to which the fresh bacteria are added after the purification process of the culture medium in a proportion of 1×10$^8$ CFU/g of product each of the following strains.

The bacteria are:
*Lactobacillus fermentum*
*Lactobacillus rhamnosus*
*Lactobacillus salivarius*
*Enterococcus faecium*

Each bacterial strain has a specific function in the canine gastrointestinal tract, broadly speaking, lactobacilli are used as probiotics since lactic acid bacteria can provide their host with physiological benefits by regulating the response of their immune system in a specific or non-specific way.

Among organic acids, acetic acid and lactic acid have the highest inhibitory activity towards Gram-negative bacteria, which are usually pathogenic and can cause diseases or conditions in the host organism.

*Lactobacillus fermentum* CCM has shown to have the ability to increase the phagocytic activity of leukocytes, as well as the phagocytic activity of neutrophils.

*Lactobacillus rhamnosus* LGG has demonstrated the ability to prevent and/or cure clinical signs of atopic dermatitis in canines of genetically predisposed and non-predisposed groups. Similarly, it decreases antibodies known as IgE, or immunoglobulin E, which is allergen specific.

*Lactobacillus salivarius* is a lactic acid bacterium that through metabolic processes inhibits the growth of *Helicobacter pylori*, which is a helical gram negative bacterium responsible for the inflammation of the GIT and the main cause of irritable bowel syndrome, an inflamed intestine prevents the settlement of certain types of beneficial bacteria given the unfavorable conditions of the stress caused by inflammation; The presence of *L. salivarius* also prevents the formation of stomach ulcers.

*Enterococcus faecium* SF68 is a microorganism that has demonstrated the ability to present an auxiliary effect in the restoration and strengthening of the intestinal mucosa in canines, this effect is useful in two ways:

By restoring the mucous membranes, it helps to create a more favorable ecosystem for other probiotics to be installed in the gastrointestinal tract.

A healthy intestinal mucosa is a relevant component to improve the immune response against GIT infections in young dogs and adults, particularly it is a desired protection mechanism in the period that a puppy stops being breastfed and is exposed to other types of food that have a strange microbiological load for its digestive system.

Using probiotic microorganisms seems to be an effective way to normalize the intestinal microbiota, especially in dogs with gastrointestinal pathogens; although stabilization in clinically healthy dogs is no less important from a preventive point of view.

The production process is carried out in the following stages:

In the first stage of the process, the culture of the bacterial species will be carried out individually in a bioreactor with stirring, temperature sensor, dissolved oxygen sensor and pH sensor, the pH will be controlled at 6.5 by the addition of NaOH and HCl; The culture medium is liquid medium. The theoretical growth time of each bacterium is described in Table 1 at 37° C.

Table 1 shows the theoretical growth time it takes for each bacterial strain to reach the optimum biomass concentration to be used in a production lot. Times may vary depending on the culture medium in which the bacteria are grown. The times presented in the table are for a simulation with liquid medium of tomato juice (10 g/L peptone, 10 g/L yeast extract, 200 mL/L tomato juice, 20 g/L glucose). Another useful medium for this process is the MRS medium and there's a wide variety of culture media suitable for growing lactobacilli.

TABLE 1

Time in hours per process.

| Process | Time per Batch [h] |
|---|---|
| *L. fermentum* growth | 10.82 |
| *L. rhamnosus* growth | 9.07 |
| *L. salivarius* growth | 7.51 |
| *Enterococcus faecium* growth | 4.26 |

Subsequently, the liquid culture is filtered through a 0.2-micron membrane using a vacuum pump and the filtrate is discarded.

During the bacterial growth, the vegetables and meats are ground until the desired food size is obtained. Similarly, some ingredients must be cooked, those that meet this characteristic should be subjected to boiling water (94.5° C.) in a pot for approximately 35 min; Once this stage is finished, all the ingredients become ground and mixed.

Likewise, while these processes are carried out, the live cricket is boiled in water at 60° C. for 3 minutes and then rinsed with cold water for 4 minutes. Finally, it is dried in a tray dryer at 80° C. with a humidity in the hot air of 0.02 kg water/kg dry air. The dry cricket is ground with the ingredients. In the event that the cricket is acquired dead and dry, these stages are avoided, it must be cleaned and passed directly to be ground.

All ground ingredients, lactobacilli, vitamins and minerals are mixed until a homogeneous mixture is obtained at room temperature.

The invention claimed is:

1. A dog superfood supplement comprising:
(a) house cricket (*Gryllodes sigillatus*), beef, cow liver, carrots, brown rice, peas, oatmeal, potato, spinach and pumpkin and
(b) vitamins and minerals,
wherein (a) and (b) are combined and ground to produce a homogeneous mixture,
wherein the homogeneous mixture further comprises
(c) four purified probiotic bacteria consisting of *Lactobacillus fermentum, Lactobacillus rhamnosus, Lactobacillus salivarius* and *Enterococcus faecium*.

2. The dog superfood supplement of claim 1, wherein the vitamins and minerals comprise vitamin A, vitamin C, vitamin D, vitamin E, vitamin K, thiamine, riboflavin, vitamin B6, vitamin B5, vitamin B12, folic acid, calcium, iron, phosphorus, iodine, magnesium, zinc, copper, manganese and selenium.

* * * * *